(12) United States Patent
Taft

(10) Patent No.: US 10,420,600 B2
(45) Date of Patent: Sep. 24, 2019

(54) ABLATION DEVICE WITH VARIABLE ASPIRATION CONTROL SYSTEM

(71) Applicant: Arthrex, Inc., Naples, FL (US)

(72) Inventor: Richard J. Taft, Naples, FL (US)

(73) Assignee: Arthrex, Inc., Naples, FL (US)

( * ) Notice: Subject to any disclaimer, the term of this patent is extended or adjusted under 35 U.S.C. 154(b) by 175 days.

(21) Appl. No.: 15/013,663

(22) Filed: Feb. 2, 2016

(65) Prior Publication Data

US 2017/0215935 A1    Aug. 3, 2017

(51) Int. Cl.
*A61B 18/14* (2006.01)
*A61B 18/00* (2006.01)
*A61B 18/04* (2006.01)
*A61B 18/16* (2006.01)

(52) U.S. Cl.
CPC ............ *A61B 18/042* (2013.01); *A61B 18/14* (2013.01); *A61B 18/16* (2013.01);
(Continued)

(58) Field of Classification Search
CPC ........... A61B 2018/00744; A61B 2018/00702; A61B 2218/002; A61B 2218/007; A61B 2018/00577
See application file for complete search history.

(56) References Cited

U.S. PATENT DOCUMENTS

| | | |
|---|---|---|
| 3,974,833 A | 8/1976 | Durden |
| 5,269,768 A | 12/1993 | Cheung |

(Continued)

FOREIGN PATENT DOCUMENTS

| | | |
|---|---|---|
| EP | 1400214 | 7/2004 |
| WO | 01/35845 | 5/2001 |
| WO | 2014137342 | 9/2014 |

OTHER PUBLICATIONS

Arthrocare, "Product Catalog", international.arthrocaresportsmedicine.com, accessed Jun. 19, 2015, document of 1 page. http://international.arthrocaresportsmedicine.com/files/International_Product_Catalog_22316_Rev_A.pdf.

(Continued)

*Primary Examiner* — Nathan R Price
*Assistant Examiner* — Tasnim Mehjabin Ahmed
(74) *Attorney, Agent, or Firm* — Akerman LLP; Michael K. Dixon

(57) ABSTRACT

An ablation device having an electrode control system configured to adjust an output of an active electrode and a variable aspiration control system configured to control aspiration in an aspiration system based upon the output of the active electrode is disclosed. In particular, the variable aspiration control system may adjust the aspiration within the aspiration system between at least a zero aspiration setting corresponding to a low ablation power setting and a high aspiration setting corresponding to a high ablation power setting, whereby a plasma field developed at the active electrode at the high ablation power setting is greater than a plasma field developed at the active electrode at the low ablation power setting. By reducing, if not, ceasing the aspiration provided by the aspiration system for the low ablation power setting, the variable aspiration control system is able to reduce the likelihood that the plasma field will be disturbed.

18 Claims, 4 Drawing Sheets

(52) U.S. Cl.
CPC ............... *A61B 2018/00577* (2013.01); *A61B 2018/00702* (2013.01); *A61B 2018/00744* (2013.01); *A61B 2018/00779* (2013.01); *A61B 2018/00892* (2013.01); *A61B 2218/002* (2013.01); *A61B 2218/007* (2013.01)

(56) References Cited

U.S. PATENT DOCUMENTS

| | | | |
|---|---|---|---|
| 5,449,357 A | 9/1995 | Zinnanti | |
| 5,524,863 A | 6/1996 | Davis | |
| 5,806,238 A * | 9/1998 | Brenner | A01M 3/005 15/339 |
| 5,830,214 A | 11/1998 | Flom et al. | |
| D412,984 S | 8/1999 | Cover et al. | |
| 6,156,025 A | 12/2000 | Niedospial et al. | |
| 6,355,032 B1 | 3/2002 | Hovda et al. | |
| 6,558,379 B1 | 5/2003 | Batchelor et al. | |
| 7,241,294 B2 | 7/2007 | Reschke | |
| 8,157,795 B2 | 4/2012 | Sartor et al. | |
| 8,241,278 B2 | 8/2012 | Sartor | |
| 8,372,067 B2 | 2/2013 | Woloszko et al. | |
| 8,685,018 B2 | 4/2014 | Cox et al. | |
| 8,715,278 B2 | 5/2014 | Toth et al. | |
| 2003/0083655 A1 | 5/2003 | Van | |
| 2003/0163126 A1 | 8/2003 | West et al. | |
| 2004/0002631 A1 | 1/2004 | Wu et al. | |
| 2011/0077643 A1 | 3/2011 | Dahla et al. | |
| 2011/0118718 A1 | 5/2011 | Toth et al. | |
| 2012/0245583 A1 | 9/2012 | Truckai | |
| 2014/0207135 A1 | 7/2014 | Hanno | |
| 2014/0257269 A1 | 9/2014 | Woloszko et al. | |
| 2014/0336630 A1 * | 11/2014 | Woloszko | A61B 18/10 606/34 |
| 2017/0112562 A1 | 4/2017 | Woloszko et al. | |

OTHER PUBLICATIONS

Medtronic, "Cardioblate BP2", www.medtronicheart.com, accessed Jun. 19, 2015, document of 12 pages. http://www.medtronicheart.com/wcm/groups/mdtcom_sg/@emanuals/@era/@cardio/documents/documents/contrib_188969.pdf.

Spencer, "Venturi surgical suction pump / vacuum-powered / fixed AS 216," www.medicalexpo.com, accessed Jun. 19, 2015, document of 1 page. http://www.medicalexpo.com/prod/spencer-italia/product-70153-427745.html.

Ridge, "Arthroscopy & Laparoscopy," Chapter 2, p. 70-84, accessed Jun. 19, 2015, document of 1 page. www.vetinst.com, http://www.vetinst.com/skin1/admin/UserFiles/File/2013%20catalogues/2013%20HI-RES%20PRICED%20CATALOGUE%20-%20PDF/Chapters/Chapter%202.pdf.

Smith & Nephew, "Coblator II Surgery System," dated Jan. 2015, document of 6 pages.

Integra, "Integra CUSA EXcel®+ Ultrasonic Tissue Ablation System", www.integralife.com, accessed Jun. 19, 2015, document of 3 pages. http://www.integralife.com/index.aspx?redir=detailproduct&Product=596&ProductName=Integra%20CUSA%20EXcel%AE%2B%20Ultrasonic%20Tissue%20Ablation%20System&ProductLineName=Tissue%20Ablation&ProductLineID=9&PA=neurosurgeon.

Lemairtre Vascular, "Trivex System Operation/Service Manual-English," eifu.lemaitre.com, dated Jul. 2014, document of 24 pages. http://eifu.lemaitre.com/ifu/active/R2601-01.Rev.B.07.14.pdf.

Stryker, "Stryker Crossfire Integrated Arthroscopy System", www.stryker.com, accessed Jun. 19, 2015, document of 1 page. http://www.stryker.com/latm/products/Endoscopy/Arthroscopy/RFAblationSystems/CrossfireIntegratedArthroscopySystem/index.htm.

Arthocare Sportsmedicine, "Introducing Quantum Coblation for Intelligent Arthroscopy," quantumcoblation.com, 2011, document of 8 pages. http://quantumcoblation.com/pdf/21223F_Quantum_Brochure.pdf.

Depuy Mitek, Inc., "Value Analysis Brief—VAPR® VUE™ with COOLPULSE® 90 Ablation Technology," synthes.vo.llnwd.net, 2011, document of 4 pages. http://synthes.vo.llnwd.net/o16/LLNWMB8/US%20Mobile/Synthes%20North%20America/Product%20Support%20Materials/Brochures/COOLPULSE_90_Value_Brief-FINAL.pdf.

European Patent Office, "European Extended Search Report and Search Opinion" issued in European Patent Application No. 17152073.7, dated Jun. 9, 2017, document of 9 pages.

\* cited by examiner

| | ABLATION SETTING | VACUUM SETTING | VSCC SETTING | |
|---|---|---|---|---|
| 26 | 9 OR HIGHER | 16-20inHG | HIGH | 24 / 42 |
| 44 | 6-8 | 10-14inHG | UPPER-MIDDLE | |
| | 4-5 | 5-9in HG | LOWER-MIDDLE | |
| 22 | 1-3 | 0-3in HG | LOW | 20 |
| | 21 | FIG. 5 | 23 | |

ABLATION DEVICE WITH VARIABLE ASPIRATION CONTROL SYSTEM

FIELD OF THE DISCLOSURE

The present disclosure generally relates to ablation devices, and more particularly to ablation devices having aspiration systems for medical procedures.

BACKGROUND

Ablation devices have been used to remove tissue within patients in a variety of medical procedures. When in use, ablation devices are often operated throughout a range of power settings. Higher power settings are often used to remove tissue via vaporization and lower settings are used for desiccation. Some ablation devices include aspiration systems to remove fluid or particulates, or both, from a surgery site within a patient. Conventional aspiration systems remove fluid and particulates from a surgery site at the same aspiration rate regardless of the power setting of the active electrode. An aspiration rate large enough to properly remove material generated at a high power setting for an active electrode is too large of an aspiration rate for a low power setting for the active electrode. In particular, the aspiration rate corresponding with the high power setting interferes with a plasma field or ionized gas vapor layer at the active electrode generated at a low power setting such as by pulling the plasma field away from the active electrode, thus affecting the behavior of the plasma field.

SUMMARY

An ablation device, such as, but not limited to, a radio frequency (RF) ablation device, with an aspiration system is disclosed. The ablation device may be a monopolar device having one or more active electrodes or a bipolar device having one or more active electrodes and one or more return electrodes that are insulated from each other. The ablation device may include an aspiration system formed integrally within the ablation device or added to the ablation device after manufacture of the device. The ablation device may include an electrode control system configured to adjust an output of the active electrode and a variable aspiration control system configured to control and vary aspiration at an opening in an aspiration system based upon the output of the active electrode is disclosed. In particular, the variable aspiration control system may be configured to adjust the aspiration within the aspiration system between at least a low aspiration setting corresponding to a low ablation power setting and a high aspiration setting corresponding to a high ablation power setting, whereby a plasma field developed at the active electrode at the high ablation power setting is greater than a plasma field developed at the active electrode at the low ablation power setting. The variable aspiration control system may also be configured to adjust the aspiration within the aspiration system between at least a zero aspiration setting corresponding to a very low ablation power setting and a high aspiration setting corresponding to a high ablation power setting, whereby a plasma field developed at the active electrode at the high ablation power setting is greater than a plasma field developed at the active electrode at the zero ablation power setting. By reducing the aspiration provided by the aspiration system to zero for the zero ablation power setting relative to the aspiration provided at the high ablation power setting, the variable aspiration control system is able to reduce the likelihood that the plasma field or ionized gas vapor layer at the active electrode will be disturbed by the aspiration system.

The ablation device may include an electrode assembly having an active electrode and an electrode control system configured to adjust the output of the active electrode between at least a low ablation power setting and a high ablation power setting. The ablation device may include an aspiration system formed from one or more aspiration conduits with an opening for aspirating material. The ablation device may include a variable aspiration control system in communication with the aspiration system and configured such that the variable aspiration control system varies an amount of aspiration at an opening within the aspiration system based upon the output of the active electrode. The variable aspiration control system may be configured to operate the aspiration system at a first aspiration rate at the low ablation power setting and at a second aspiration rate at the high ablation power setting, wherein the second aspiration rate at the high ablation power setting is greater than the first aspiration rate at the low ablation power setting.

The ablation device may include an electrode assembly having an active electrode and an electrode control system configured to adjust the output of the active electrode between at least a low ablation power setting and a high ablation power setting. The ablation device may include an aspiration system formed from at least one aspiration conduit with an opening for aspirating material and a variable aspiration control system in communication with the aspiration system and configured such that the variable aspiration control system varies an amount of aspiration at an opening within the aspiration system based upon the output of the active electrode. The variable aspiration control system may be configured to operate the aspiration system at a first aspiration rate, such as but not limited to zero aspiration, at the low ablation power setting and at a second aspiration rate at the high ablation power setting, whereby the second aspiration rate at the high ablation power setting is greater than the first aspiration rate at the low ablation power setting. The variable aspiration control system may be formed from a first body having one or more first body orifices and a second body having one or more second body orifices, whereby one or more of the first and second bodies is movable relative to the other such that alignment between the first and second body orifices can be varied to change the aspiration within the aspiration system.

A method of using the ablation device may include providing power to an active electrode of an electrode assembly of an ablation device formed from the active electrode and an electrode control system configured to adjust the output of the active electrode between at least a low ablation power setting and a high ablation power setting. The ablation device may be formed from an aspiration system formed from one or more aspiration conduits with an opening for aspirating material and a variable aspiration control system in communication with the aspiration system and configured such that the variable aspiration control system varies an amount of aspiration at an opening within the aspiration system based upon the output of the active electrode. The method may also include adjusting, via the variable aspiration control system, the aspiration at an opening in the aspiration system.

These and other embodiments are described in more detail below.

BRIEF DESCRIPTION OF THE DRAWINGS

The accompanying drawings, which are incorporated in and form a part of the specification, illustrate embodiments of the presently disclosed invention and, together with the description, disclose the principles of the invention.

FIG. 5 is a table of sample ablation device active electrode power settings and corresponding aspiration settings and vacuum settings.

DETAILED DESCRIPTION

Figure 1:
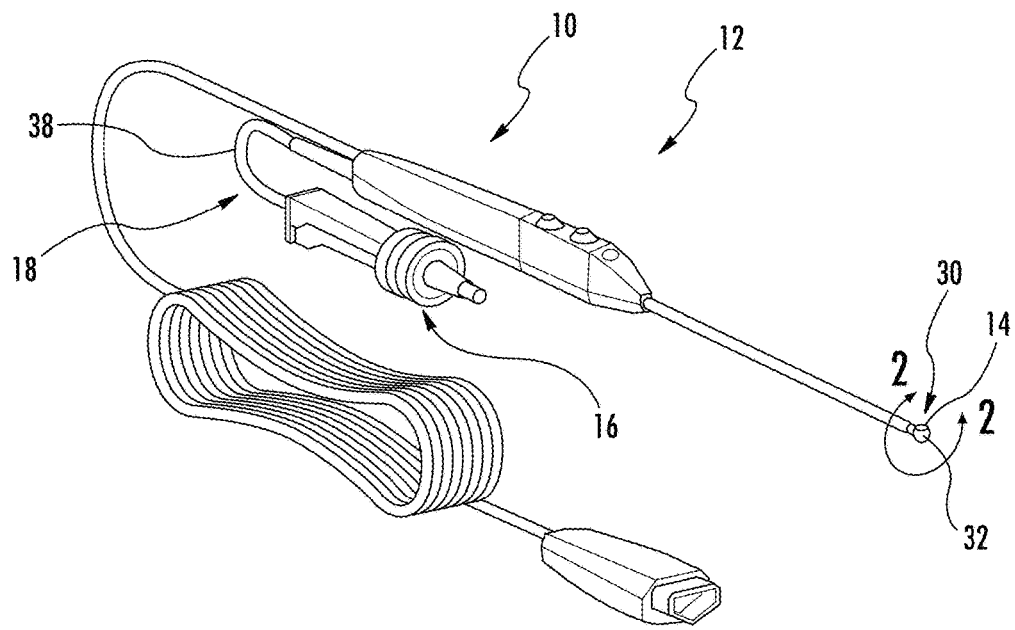
FIG. 1 is a perspective view of an ablation device including an aspiration system and a variable aspiration control system.
Figure 2:
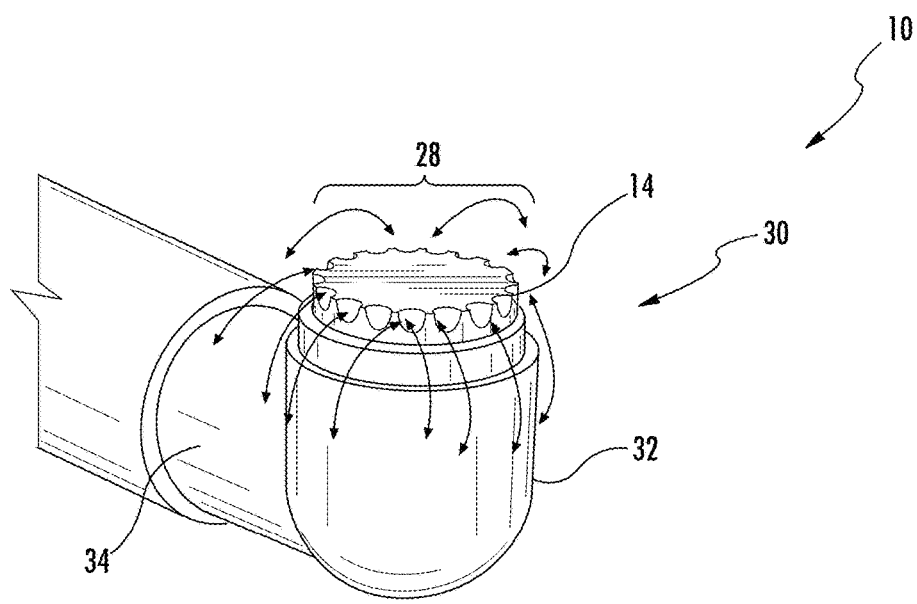
FIG. 2 is a detail perspective view of active and return electrodes at a distal end of the ablation device with a plasma layer and including the aspiration system and the variable aspiration control system taken at detail 2-2 in FIG. 1.

As shown in FIGS. 1-13, an ablation device 10 with an aspiration system 18 is disclosed. The ablation device 10 may include an electrode control system 12 configured to adjust an output of an active electrode 14 and a variable aspiration control system 16 configured to control and vary aspiration at an opening in an aspiration system 18 based upon the output of the active electrode 14. In particular, the variable aspiration control system 16 may be configured to adjust the aspiration within the aspiration system 18 between at least a zero aspiration setting 80 corresponding to a low ablation power setting 22 and a high aspiration setting 24 corresponding to a high ablation power setting 26, whereby a plasma field 28 developed at the active electrode 14 at the high ablation power setting 26 is greater than a plasma field 28 developed at the active electrode 14 at the low ablation power setting 22. By reducing, and in some cases, ceasing aspiration provided by the aspiration system 18 for the low ablation power setting 22 relative to the aspiration provided at the high ablation power setting 26, the variable aspiration control system 16 is able to reduce the likelihood that the plasma field 28 at the active electrode 14 will be disturbed by the aspiration system 18.

The ablation device 10 may include an electrode assembly 30 having one or more active electrodes 14. The active electrode 14 may be positioned at a distal end 32 of the ablation device 10, in close proximity to the distal end 32, or in another location. The active electrode 14 may have any appropriate shape and is not limited to a particular shape or arrangement for purposes of the ablation device 10. The ablation device 10 may be configured to operate in any appropriate manner, such as, but not limited to, as a monopolar device. Alternatively, the ablation device 10 may be configured to operate as a bipolar device. As such, the ablation device 10 may include one or more return electrodes 34 positioned proximate to the active electrode 14. One or more of the return electrodes 34 may be positioned in close proximity to the active electrode 14. The ablation device 10 may include any number of return electrodes 34 that may be greater than, equal to or less than a number of active electrodes 14. The return electrode 34 may have any appropriate configuration. The active electrode 14 may be insulated from the return electrode 34 in any appropriate manner and using appropriate materials.

The ablation device 10 may include an electrode control system 12 configured to control the output of the active electrode 14 to adjust the output of the active electrode between at least a zero ablation power setting and a high ablation power setting. The electrode control system 12 may include any appropriate power source, such as, but not limited to, a radio frequency (RF) generator, or may be configured to be coupled to an appropriate power source. The electrode control system 12 may visually display power supplied to the active electrode 14. The manner in which the electrode control system 12 may visually display power supplied to the active electrode 14 is not limited to one particular system, but may include displaying the amount of power supplied to the active electrode 14 on a graphical user interface (GUI), such as, but not limited to, a display on the ablation device 10, a support structure for the ablation device 10, mobile devices, tablets, phablets, laptop personal computers (PC), desktop PCs, smartphones, other computing devices and the like. The electrode control system 12 may include a digital display or analog display of the power output of the active electrode 14, or both. The electrode control system 12 may include ablation settings between 1 and 10 or much higher than 10. As shown in FIG. 5, the ablation settings 21 up to and including 3 may be considered a low ablation power setting 23. The ablation settings 22 of 4 and 5 may be considered a lower middle ablation power setting 20. The ablation settings 44 of 6, 7 and 8 may be considered an upper middle ablation power setting 42. The ablation settings 26 greater than and including 9 may be considered a high ablation power setting 24. The power settings of the electrode control system 12 are not limited to this manner of power delineation but may be delineated in other manners as well.

Figures 3, 4:
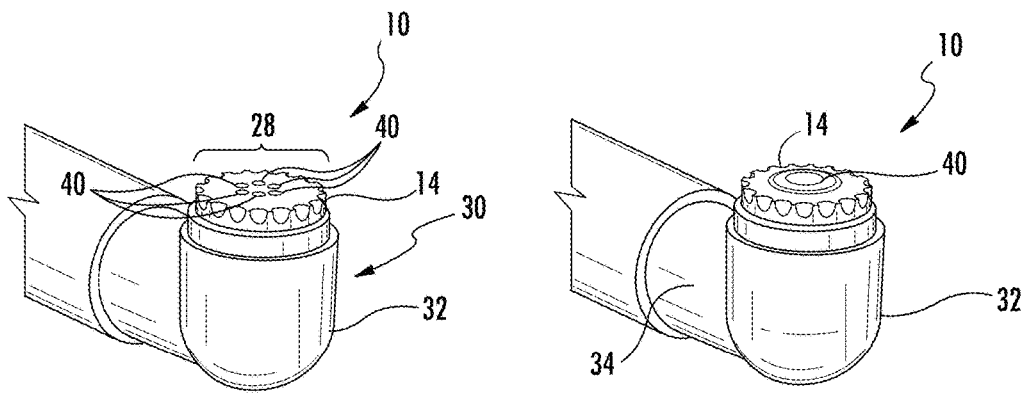
FIG. 3 is a detail perspective view of the active and return electrodes of FIG. 2 shown with a plurality of openings for the aspiration system.
FIG. 4 is a detail perspective view of the active and return electrodes of FIG. 2 shown with a single opening for the aspiration system.

The ablation device 10 may include an aspiration system 18, as shown in FIGS. 1-4, formed from one or more aspiration conduits 38 with an opening 40 for aspirating material. The aspiration system 18 may include a single opening 40, as shown in FIG. 4, or a plurality of openings 40, as shown in FIG. 3. In at least one embodiment, as shown in FIG. 3, the aspiration system 18 may include six openings 40 forming a ring on the active electrode 14. The aspiration conduit 38 may have any appropriate cross-sectional shape and configuration. The aspiration conduit 38 may be integrally formed within the ablation device 10. Alternatively, the aspiration conduit 38 may be attached outside of the ablation device 10, such as being added after manufacture of the ablation device 10. The aspiration system 18 may or may not include an aspiration generator, such as a vacuum source, pump or the like. If the aspiration system 18 does not include an aspiration generator, the aspiration system 18 may be configured to be attached, via one or more releasable connectors or one or more permanent connections, to one or more aspiration generators.

The ablation device 10 may include a variable aspiration control system 16, as shown in FIGS. 1, 6-10 and 13, in communication with the aspiration system 18 and configured such that the variable aspiration control system 16 varies an amount of aspiration at an opening within the aspiration system 18 based upon the output of the active electrode 14. FIGS. 6-10 disclose a rotary variable aspiration control system 16 and FIG. 13 discloses a linear variable aspiration control system 16. The variable aspiration control system 16 may be configured to operate the aspiration system 18 at a first low aspiration rate 23 at the low ablation power setting 21 and at a second high aspiration rate 24 at the high second ablation power setting 26. The second high aspiration rate 24 at the high ablation power setting 26 may be greater than the first low aspiration rate 23 at the low ablation power setting 21. The electrode control system 16 may be configured to adjust the output of the active electrode 14 between at least a low ablation power setting 21 and a high ablation power setting 24 in which the plasma field 28 developed at the active electrode 14 is greater than produced at the low ablation power setting 21. The variable aspiration control system 16 may be configured to operate the aspiration system 18 along a continuum between and including a first low aspiration rate 23 at the low ablation power setting 22 and at a second high aspiration rate 24 at the high ablation power setting 26. The second high aspiration rate 24 at the high ablation power setting 26 may be greater than the first low aspiration rate 23 at the low ablation power setting 21. The variable aspiration control system 16 may be configured to operate, but is not limited to operating, the aspiration system 18 at a first low aspiration rate 23 between about 0 inches of mercury and 3 inches of mercury when the electrode control system 12 is positioned at a lower quarter level of power output 21 of the active electrode 14. The variable aspiration control system 16 may be configured to operate, but is not limited to operating, the aspiration system 18 at a second high aspiration rate 24 between about 16 inches of mercury and 20 inches of mercury when the electrode control system 12 is positioned at a high level of power output 26 of the active electrode 14. The variable aspiration control system 16 may be configured to operate, but is not limited to operating, the aspiration system 18 at a third aspiration rate 22 between about 5 inches of mercury and 9 inches of mercury when the electrode control system 12 is positioned at a lower middle level of power output 20 of the active electrode 14. The variable aspiration control system 16 may be configured to operate, but is not limited to operating, the aspiration system 18 at a fourth aspiration rate 44 between about 10 inches of mercury and 14 inches of mercury when the electrode control system 12 is positioned at an upper middle level of power output 42 of the active electrode 14.

The variable aspiration control system 16 may be operated manually by one or more users, automatically via the variable aspiration control system 16, or a combination of both. The variable aspiration control system 16 may be configured to operate the aspiration system 18 automatically based upon the power output of the active electrode 14.

Figure 6:
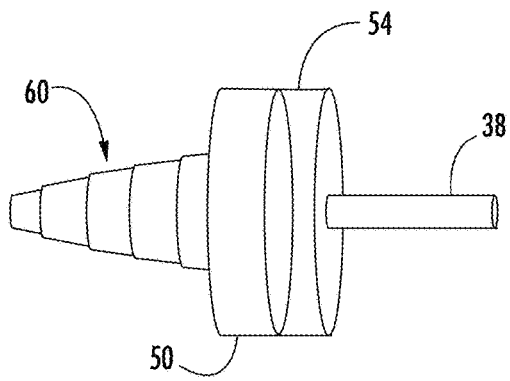
FIG. 6 is perspective view of a rotary variable aspiration control system having a first body with first body orifices and a second body with second body orifices.
Figure 7:
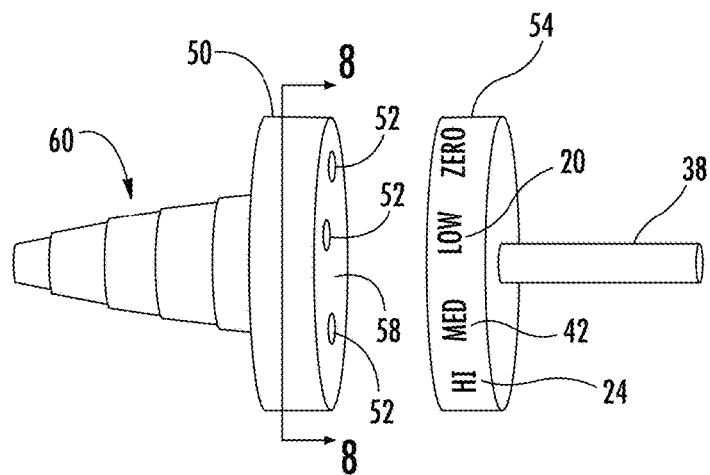
FIG. 7 is an exploded view of the variable aspiration control system of FIG. 6.

The variable aspiration control system 16 may be formed from one or more components configured to control the rate of aspiration through one or more openings 40 of the aspiration system 18. The variable aspiration control system 16 is not limited to any particular configuration. As shown in FIGS. 6-10, the variable aspiration control system 16 may be formed from a first body 50 having one or more first body orifices 52 and a second body 54 having one or more second body orifices 56. The first and second bodies 52, 56 may be movable relative to the other such that alignment between the first and second body orifices 52, 56 can be varied to change the aspiration within the aspiration system 18. As such, the first and second bodies 52, 56 may be rotatable relative to the other such that alignment between the first and second body orifices 52, 56 can be varied to change the aspiration within the aspiration system 18. The first body 50 may be formed from a disc having one or more first body orifices 52, such as one first body orifice 52 or a plurality of first body orifices 52. The second body 56 may be formed from a disc having one or more second body orifices 56, such as one second body orifice 56 or a plurality of second body orifices 56. The first body 50 or second body 56, or both, may include a connector 60 enabling the first body orifices 52 or the second body orifices 56 to be attached to be coupled to aspiration conduits 38. The first body orifices 52, as shown in FIGS. 6 and 7, may be in fluid communication with the aspiration conduits 38 via one or more aspiration manifolds (not shown) within the first body 50. The second body orifices 56 may be in fluid communication with the aspiration conduits 38 via one or more aspiration manifolds (not shown) within the second body 54.

Figure 8:
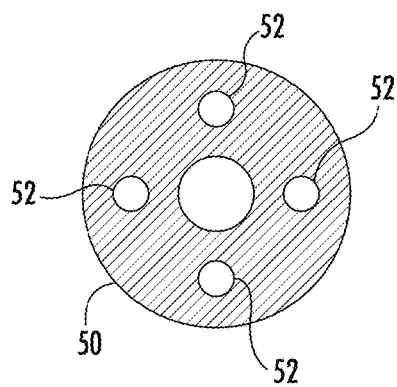
FIG. 8 is a cross-sectional view of the first body taken at section line 8-8 in FIG. 7 and showing the first body orifices aligned with the second body orifices creating a high aspiration rate within the aspiration system.
Figure 9:
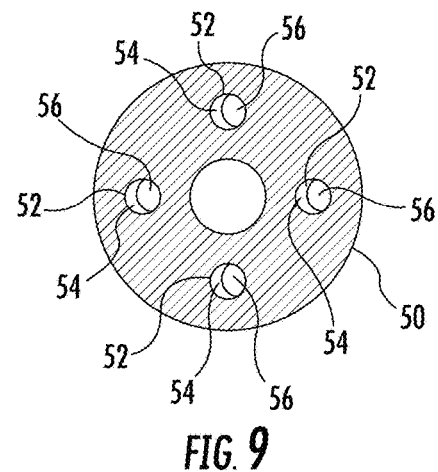
FIG. 9 is a cross-sectional view of the first body taken at section line 8-8 in FIG. 7 and showing the first body orifices partially aligned with the second body orifices creating an medium aspiration rate within the aspiration system, which is less than the aspiration rate found in the configuration in FIG. 8.
Figure 10:
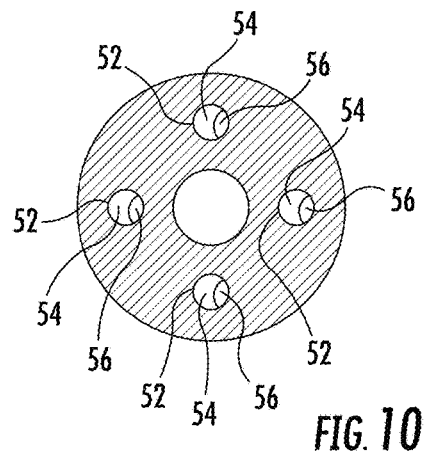
FIG. 10 is a cross-sectional view of the first body taken at section line 8-8 in FIG. 7 and showing the first body orifices less partially aligned with the second body orifices than in FIG. 9, thereby creating a low aspiration rate within the aspiration system which is less than the aspiration rate found in the configuration in FIG. 9.
Figure 11:
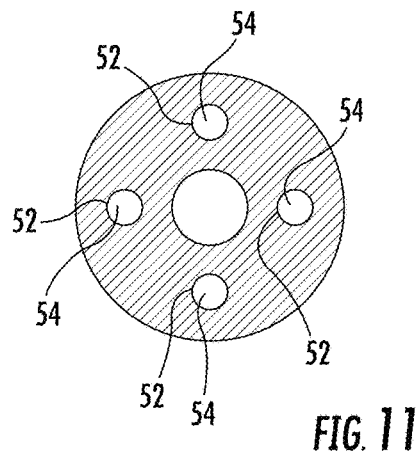
FIG. 11 is a cross-sectional view of the first body taken at section line 8-8 in FIG. 7 and showing the first body orifices completely misaligned with the second body orifices, thereby closing the first body orifices and creating a zero aspiration rate within the aspiration system which is less than the aspiration rate found in the configuration in FIG. 10.

At least a portion of each first body orifice 52 of the first body 50 may be aligned with at least a portion of each second body orifice 56 of the second body 54 when the first body 50 is positioned in a single position relative to the second body 54. The variable aspiration control system 16 may be configured such that each first body orifice 52 of the first body 50 is aligned with each second body orifice 56 of the second body 54 when the first body 50 is positioned in a single position relative to second body 54, as shown in FIG. 8. When the variable aspiration control system 16 is positioned in the range of delivering the upper middle level of output power 44, one or more of the first body orifices 52 may be misaligned with the second body orifices 56, as shown in FIG. 9. When the variable aspiration control system 16 is positioned, as shown in FIG. 10, in the range of delivering the lower middle ablation power setting 22, one or more of the first body orifices 52 may be more misaligned with the second body orifices 56 than the middle level of output power 44 position in FIG. 9. When the variable aspiration control system 16 is positioned, as shown in FIG. 11, in the range of delivering the low ablation power setting 22, the first body orifices 52 may be completely misaligned with the second body orifices 56 resulting in zero to very low aspiration.

The variable aspiration control system 16 may be configured such that the plurality of first body orifices 52 of the first body 50 are equal in number to the plurality of second body orifices 56 of the second body 54, or the plurality of first body orifices 52 of the first body 50 may be greater than or less than a number of the plurality of second body orifices 56 of the second body 54. The plurality of first body orifices 52 of the first body 50 may have cross-sectional shapes that are equivalent to cross-sectional shapes of the plurality of second body orifices 56 of the second body 54, as shown in FIG. 8. Alternatively, the plurality of first body orifices 52 of the first body 50 may have cross-sectional shapes that are different to cross-sectional shapes of the plurality of second body orifices 56 of the second body 54.

Figure 13:
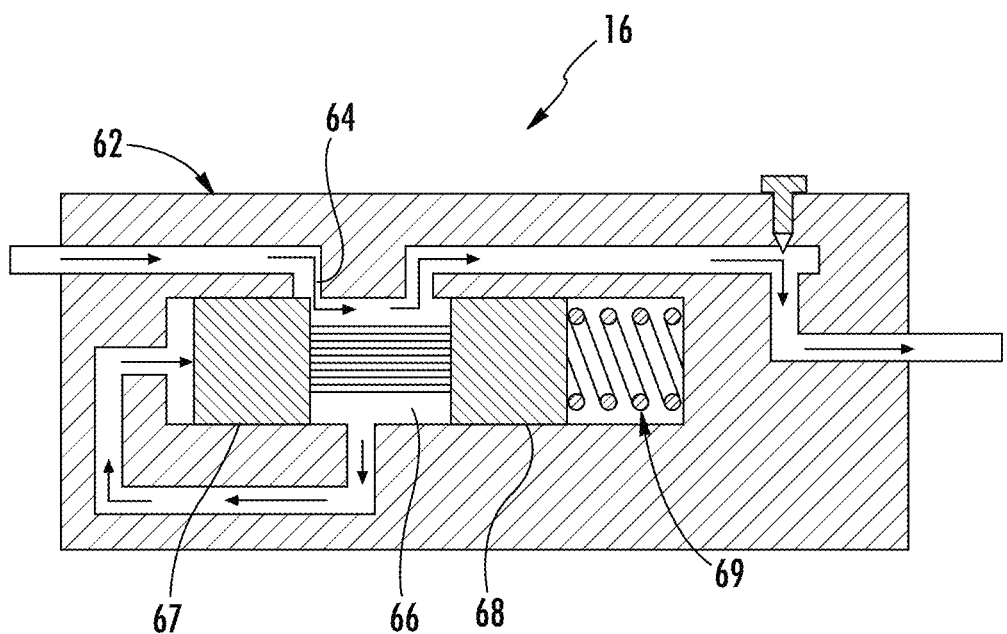
FIG. 13 is a cross-sectional side view of a linear variable aspiration control system usable with the ablation device.

As shown in FIG. 13, the variable aspiration control system 16 may be formed from a linear control system. The linear variable aspiration control system 16 may be configured such that aspiration is controlled via linear movement of a flow control member 62 that either completely blocks, partially opens or fully opens one or more orifices 64 within a control chamber 66. As such, movement of the flow control member 62 relative to the one or more orifices 64 enables the flow control member 62 to be moved from a position in which all aspects of the orifice 64 are not blocked to a position in which the all of the orifices 64 are completely blocked, including all positions in between. The flow control member 62 may be moved linearly via any appropriate manner, including, but not limited to, mechanical systems, including manual and automated systems, electromechanical systems. In at least one embodiment, a first flow control member 67 may move linearly based upon the movement of a second flow control member 68. The first flow control member 67 may be biased towards the second flow control member 68 with one or more springs 69. The position of the first flow control member 67 may be controlled via a solenoid (not shown) or a mechanical device, such as a threaded bolt. As the position of the first flow control member 67 changes, electromagnetic fields may move the second flow control member 68, thereby changing the coverage of the orifice 64 and changing the aspiration.

Figure 12:
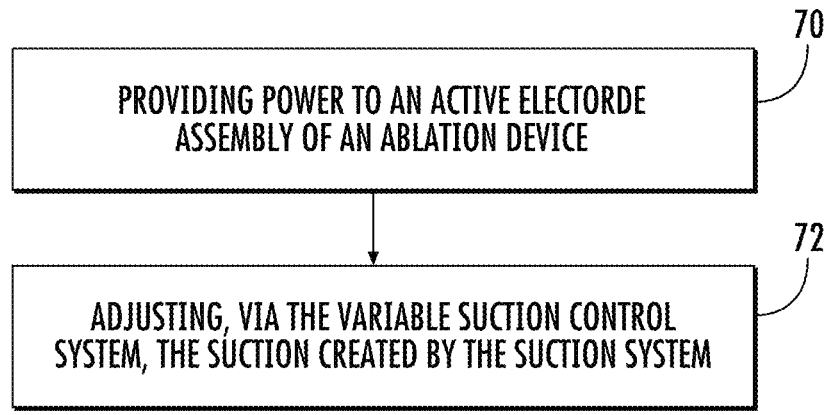
FIG. 12 is a flow diagram of a method of using the ablation device of FIGS. 1-11.

A method, as shown in FIG. 12, of using the ablation device 10 may include providing power at 70 to an active electrode 14 of an electrode assembly of the ablation device 10. The ablation device 10 may be configured as previously set forth, such as including an active electrode 14. The ablation device 10 may or may not include a return electrode 34 on the ablation device, whereby the active electrode 14 may be insulated from the return electrode 34. The ablation device 10 may include an electrode control system 12 configured to adjust the output of the active electrode 14 between at least a low ablation power setting 22 and a high ablation power setting 26. The ablation device 10 may also include an aspiration system 18 formed from one or more aspiration conduits 38 with an opening 40 for aspirating material. The ablation device 10 may include a variable aspiration control system 16 in communication with the aspiration system 18 and configured such that the variable aspiration control system 16 varies an amount of aspiration at an opening within the aspiration system 18 based upon the output of the active electrode 14. The method of using the ablation device 10 may include adjusting, via the variable aspiration control system at 72, the aspiration at an opening in the aspiration system 18. Adjusting the aspiration at 72 at an opening in the aspiration system 18 may include the variable aspiration control system 16 automatically adjusting the aspiration at an opening in the aspiration system 18 based upon the output of the active electrode 14. The variable aspiration control system 16 may change the alignment of one or more first body orifices 52 in relation to one or more second body orifices 56. The variable aspiration control system 16 may rotate the first body orifice 52 in relation to one or more second body orifices 56, or vice versa. The first body orifice 52 may be positioned on an upstream side of an interface 58 between the first and second bodies 50, 54. The variable aspiration control system 16 may rotate the first body orifice 52 in relation to one or more second body orifices 56, or vice versa, via a drive motor or other device or may require a user to manually rotate the components. Maximum aspiration at the opening 40 may be achieved when all first body orifices 52 of the first body 50 are aligned with all second body orifices 56 of the second body 54, as shown in FIG. 8. The first and second bodies 50, 54 may have any appropriate configuration with mating faces.

The ablation device 10 may be configured to enable a variable aspiration control system 16 configured to control and vary aspiration at an opening in an aspiration system 18 based upon the output of the active electrode 14. As such, the aspiration rate does not remain constant throughout the range of power settings 21, 22, 26, 44 corresponding to various levels of power supplied to the one or more active electrodes 14. Instead, the aspiration is varied based upon the size of the plasma field 28 formed at the active electrode 14, which directly corresponds to the power supplied to the one or more active electrodes 14. The higher the power level provided to an active electrode 14, the greater the plasma field 28 formed around the active electrode 14. The lower the power level provided to an active electrode 14, the smaller the plasma field 28 formed around the active electrode 14. To protect the plasma field 28 formed around the active electrode 14 at lower power levels, the variable aspiration control system 16 is configured to reduce the aspiration rate at the opening 40 to reduce the aspiration at the plasma field 28. As such, the plasma field 28 may remain intact at the active electrode even when aspiration is presented by the ablation device 10.

The foregoing is provided for purposes of illustrating, explaining, and describing embodiments of this invention. Modifications and adaptations to these embodiments will be apparent to those skilled in the art and may be made without departing from the scope or spirit of this invention.

We claim:

1. An ablation device, comprising:
   an electrode assembly having an active electrode and a return electrode, wherein the active electrode is insulated from the return electrode;
   an electrode control system configured to adjust an output of the active electrode between at least a low ablation power setting and a high ablation power setting;
   an aspiration system formed from at least one aspiration conduit with an opening for aspirating material; and
   a variable aspiration control system in communication with the aspiration system and configured such that the variable aspiration control system varies an amount of aspiration at the opening within the aspiration system based upon the output of the active electrode and wherein ranges of aspiration correlating to ablation power settings are distinct and non-overlapping for each power setting.

2. The ablation device of claim 1, wherein the variable aspiration control system is configured to operate the aspiration system at a first aspiration rate at the low ablation power setting and at a second aspiration rate at the high ablation power setting, wherein the second aspiration rate at the high ablation power setting is greater than the first aspiration rate at the low ablation power setting.

3. The ablation device of claim 1, wherein the electrode control system is configured to adjust the output of the active electrode between at least a low ablation power setting and a high ablation power setting in which a plasma field developed at the active electrode is greater than another plasma field produced at the low ablation power setting.

4. The ablation device of claim 1, wherein the variable aspiration control system is configured to operate the aspiration system along a continuum between and including a first aspiration rate at the low ablation power setting and a second aspiration rate at the high ablation power setting, wherein the second aspiration rate at the high ablation power setting is greater than the first aspiration rate at the low ablation power setting.

5. The ablation device of claim 1, wherein the variable aspiration control system is configured to operate the aspiration system automatically based upon the power output of the active electrode.

6. The ablation device of claim 1, wherein the variable aspiration control system is formed from a first body having at least one first body orifice and a second body having at least one second body orifice, wherein the first body is movable relative to the second body such that alignment between the at least one first and second body orifices can be varied to change the aspiration within the aspiration system.

7. The ablation device of claim 6, wherein the at least one first body is formed from a disc having the at least one first body orifice.

8. The ablation device of claim 7, wherein the at least one first body is a disc having a plurality of first body orifices.

9. The ablation device of claim 8, wherein the at least one second body is formed from a disc having the at least one second body orifice.

10. The ablation device of claim 9, wherein the at least one second body is a disc having a plurality of second body orifices.

11. The ablation device of claim 10, wherein at least a portion of each first body orifice of the at least one first body is aligned with at least a portion of each second body orifice of the at least one second body when the at least one first body is positioned in a single position relative to the at least one second body.

12. The ablation device of claim 10, wherein each first body orifice of the at least one first body is aligned with each second body orifice of the at least one second body when the at least one first body is positioned in a single position relative to the at least one second body.

13. The ablation device of claim 10, wherein the plurality of first body orifices of the at least one first body are equal in number to the plurality of second body orifices of the at least one second body.

14. The ablation device of claim 13, wherein the plurality of first body orifices of the at least one first body have cross-sectional shapes that are equivalent to cross-sectional shapes of the plurality of second body orifices of the at least one second body.

15. An ablation device, comprising:
an electrode assembly having an active electrode and a return electrode, wherein the active electrode is insulated from the return electrode;
an electrode control system configured to adjust an output of the active electrode between at least a low ablation power setting and a high ablation power setting;
an aspiration system formed from at least one aspiration conduit with an opening for aspirating material;
a variable aspiration control system in communication with the aspiration system and configured such that the variable aspiration control system varies an amount of aspiration at an opening within the aspiration system based upon the output of the active electrode and wherein ranges of aspiration correlating to ablation power settings are distinct and non-overlapping for each power setting;
wherein the variable aspiration control system is configured to operate the aspiration system at a first aspiration rate at the low ablation power setting and at a second aspiration rate at the high ablation power setting, wherein the second aspiration rate at the high ablation power setting is greater than the first aspiration rate at the low ablation power setting; and
wherein the variable aspiration control system is formed from a first body having at least one first body orifice and a second body having at least one second body orifice, wherein at least one of the first and second bodies is movable relative to the other such that alignment between the at least one first and second body orifices can be varied to change the aspiration within the aspiration system.

16. The ablation device of claim 15, wherein the at least one first body is formed from a disc having a plurality of first body orifices, wherein the at least one second body is formed from a disc having a plurality of second body orifices, and wherein at least a portion of each first body orifice of the at least one first body is aligned with at least a portion of each second body orifice of the at least one second body when the at least one first body is positioned in a single position relative to the at least one second body.

17. A method, comprising:
providing power to an active electrode of an electrode assembly of an ablation device comprising:
the active electrode and a return electrode, wherein the active electrode is insulated from the return electrode;
an electrode control system configured to adjust an output of the active electrode between at least a low ablation power setting and a high ablation power setting;
an aspiration system formed from at least one aspiration conduit with an opening for aspirating material; and
a variable aspiration control system in communication with the aspiration system and configured such that the variable aspiration control system varies an amount of aspiration at the opening within the aspiration system based upon the output of the active electrode and wherein ranges of aspiration correlating to ablation power settings are distinct and non-overlapping for each power setting; and
adjusting, via the variable aspiration control system, the aspiration at the opening of the aspiration system.

18. The method of claim 17, wherein adjusting the aspiration at the opening of the aspiration system comprises the variable aspiration control system automatically adjusting the aspiration at the opening of the aspiration system based upon the output of the active electrode.

* * * * *